United States Patent
Lai et al.

(10) Patent No.: US 11,299,504 B2
(45) Date of Patent: Apr. 12, 2022

(54) PROCESS FOR PREPARING A TRIAZINE-BASED PRECURSOR, THE PRECURSOR PREPARED THEREBY, A METHOD FOR PRODUCING A MICRO-PARTICULATE COMPLEX USING THE PRECURSOR, AND THE MICRO-PARTICULATE COMPLEX PRODUCED THEREBY

(71) Applicants: National Chi Nan University, Nantou (TW); Great Chain Chemical Ltd., Taipei (TW)

(72) Inventors: Long-Li Lai, Taichung (TW); Cheng-Hua Lee, Nantou (TW); Jhih-Yuan Tong, Nantou (TW); Yan-Chih Lu, Nantou (TW); Yu-You Lin, Nantou (TW); Ya-Lin Chang, Nantou (TW)

(73) Assignees: NATIONAL CHI NAN UNIVERSITY, Puli (TW); GREAT CHAIN CHEMICAL LTD, Taipei (TW)

( * ) Notice: Subject to any disclaimer, the term of this patent is extended or adjusted under 35 U.S.C. 154(b) by 3 days.

(21) Appl. No.: 16/988,775

(22) Filed: Aug. 10, 2020

(65) Prior Publication Data

US 2020/0369687 A1 Nov. 26, 2020

Related U.S. Application Data

(62) Division of application No. 15/977,391, filed on May 11, 2018, now abandoned.

(30) Foreign Application Priority Data

Aug. 15, 2017 (TW) .................................. 106127601

(51) Int. Cl.
| | |
|---|---|
| *C07D 251/46* | (2006.01) |
| *C07F 7/08* | (2006.01) |
| *C07D 251/26* | (2006.01) |
| *C07D 251/52* | (2006.01) |
| *C07D 251/54* | (2006.01) |
| *C07F 7/18* | (2006.01) |

(52) U.S. Cl.
CPC .......... *C07F 7/0812* (2013.01); *C07D 251/26* (2013.01); *C07D 251/46* (2013.01); *C07D 251/52* (2013.01); *C07D 251/54* (2013.01); *C07F 7/1804* (2013.01)

(58) Field of Classification Search
CPC ... C07D 251/46; C07D 251/52; C07D 251/56
USPC ................... 544/194, 196, 204, 219
See application file for complete search history.

(56) References Cited

U.S. PATENT DOCUMENTS

| 2,949,434 | A | 8/1960 | Pike et al. |
|---|---|---|---|
| 8,263,766 | B2 | 9/2012 | Tsuchida |
| 9,790,242 | B2 | 10/2017 | Mori et al. |
| 2011/0003989 | A1 | 1/2011 | Tsuchida |
| 2015/0152124 | A1 | 6/2015 | Mori et al. |

FOREIGN PATENT DOCUMENTS

| CN | 101433826 A | 5/2009 |
|---|---|---|
| CN | 102952157 A | 3/2013 |
| CN | 102952158 A | 3/2013 |
| CN | 103910755 A | 7/2014 |
| GB | 1466992 A | 3/1997 |
| TW | 201510050 A | 3/2015 |

OTHER PUBLICATIONS

Search Report appended to an Office Action, which was issued to Taiwanese counterpart application No. 106127601 by the TIPO dated Dec. 26, 2017, with an English translation thereof.
Rao et al. CN 103910755,Jul. 9, 2014; CA 161: 216409,2014. CAPLUS Abstract provided.
Ghiaci et al. RSC Advances (2014), 4(30), 15496-15501; CA 162; 413189, 2014. CAPLUS Abstract provided.
Niembro et al. New Journal of Chemistry (2013), 37(2), 278-282; CA 158: 218679, 2013. CAPLUS Abstract provided.
Niebro et al. ARKIVOC 2010 (iii) 181-190.
Liang et al. CN 101433826, May 20, 2009; CA 151: 69309, 2009. CAPLUS Abstract provided.
Niembro Sandra et al. Organic Letters (2008), 10(15), 3215-3218.
Kairies et al. Organosilicon Chemistry 111: From Molecules to Materials, [Muenchner Silicontage], 3rd, Munich, Apr. 1996 ( 1998), Meeting Date 1996, 543-549: CA 128: 181964, 1998. CAPLUS Abstract provided.
CN 102952158, Mar. 6, 2013, English Machine Translation, Oct. 15, 2018 provided.
Search Report appended to an Office Action, which was issued to Chinese counterpart application No. 201810914631.2 by the CNIPA dated Aug. 11, 2021, with an English translation thereof.
CAS RN 203578-79-4, STN Registry, Apr. 2, 1998.
Mehran Ghiaci et al., "Preparation, characterization and first application of silica supported palladium-N-heterocyclic carbene as a heterogeneous catalyst for C-C coupling reactions," RSC Advances, vol. 4, Mar. 13, 2014, pp. 15496-15501.

*Primary Examiner* — Deepak R Rao
(74) *Attorney, Agent, or Firm* — Husch Blackwell LLP

(57) ABSTRACT

A process for preparing a triazine-based precursor for producing a micro-particulate complex containing a far infrared-emissive silica particle comprises steps of: a) subjecting 2-4-6-trichloro-1,3,5-triazine and a first nucleophilic compound to a displacement reaction in the presence of a first solvent at a first temperature range to form an intermediate; and b) subjecting the intermediate and a second nucleophilic compound to a further displacement reaction in the presence of a second solvent at a second temperature range higher than the first temperature range.

2 Claims, No Drawings

PROCESS FOR PREPARING A TRIAZINE-BASED PRECURSOR, THE PRECURSOR PREPARED THEREBY, A METHOD FOR PRODUCING A MICRO-PARTICULATE COMPLEX USING THE PRECURSOR, AND THE MICRO-PARTICULATE COMPLEX PRODUCED THEREBY

CROSS-REFERENCE TO RELATED APPLICATION

This application claims priority of Taiwanese Application No. 106127601, filed on Aug. 15, 2017.

FIELD

The disclosure relates to a process for preparing a triazine-based precursor, and more particularly to a process for preparing a triazine-based precursor for producing a micro-particulate complex containing a far infrared-emissive silica particle. The disclosure also relates to the triazine-based precursor prepared by the process, a method for producing a micro-particulate complex containing a far infrared-emissive silica particle using the triazine-based precursor, and the micro-particulate complex produced thereby.

BACKGROUND

US 2015/0152124 discloses a surface treatment agent which is a compound of Formula (A) or Formula (B):

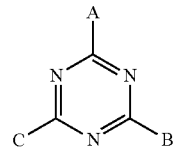
(A)

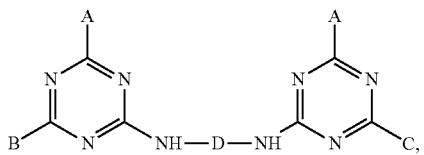
(B)

wherein A, B, C, and D are as defined therein.

The surface treatment agent has diverse functions for treatment of substrates made of various materials. However, when the surface treatment agent is subjected to a reaction with tetraethyl orthosilicate form to a complex containing a silica particle, the complex thus formed has an undesirably wide particle size distribution. Specifically, as shown below, when the surface treatment agent of Formula B (in which A is —NHR, each of B and C is —Si $(EtO)_3$, and D is —$R_2$—) is subjected to a reaction with tetraethyl orthosilicate, the complex thus formed has various configurations, and accordingly has an undesirably wide particle size distribution.

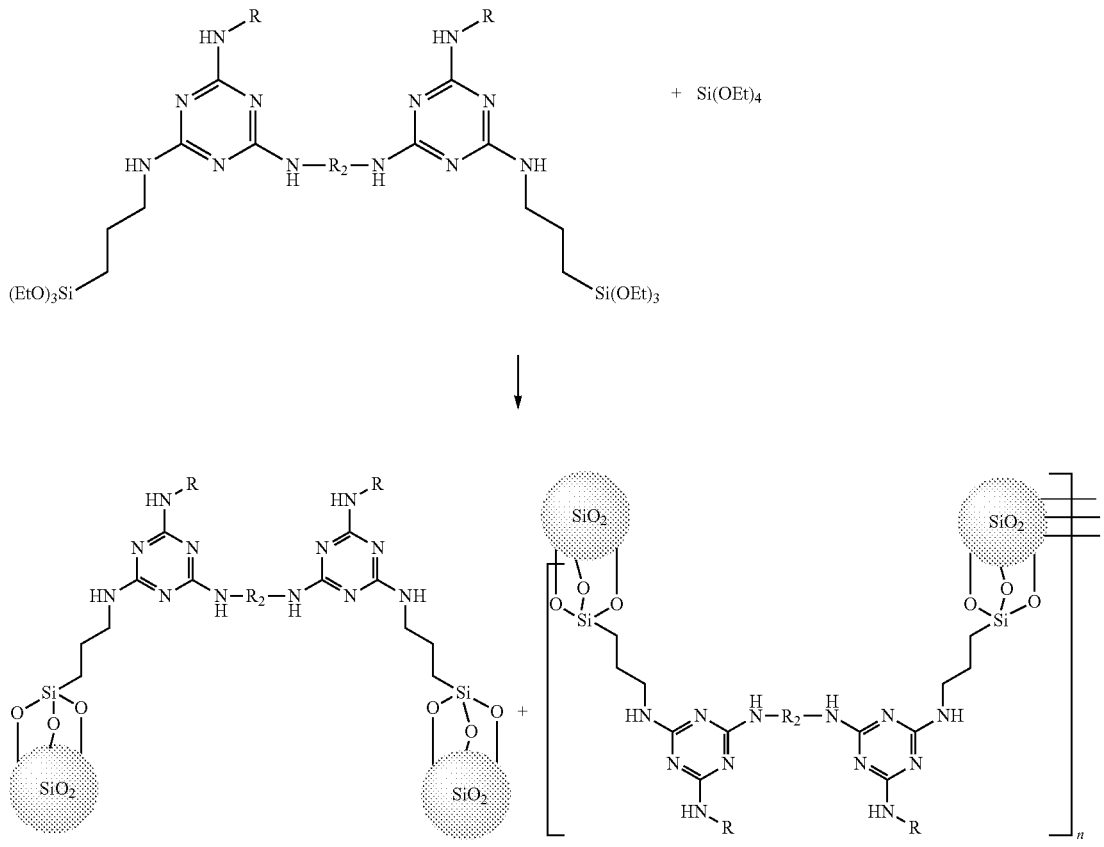

(n is an integer greater than 2)

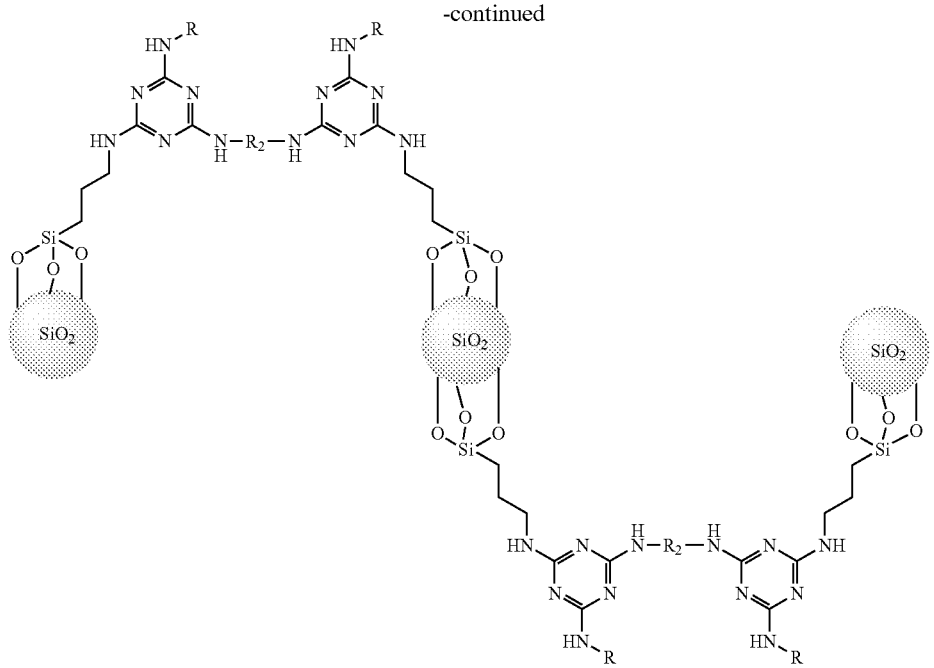

When the complex is used for cosmetic and/or medical products, it cannot be dispersed in the products evenly.

An article entitled "Fluoroalkyl Silane Modified Silicone Rubber/Nanoparticle Composite: A Super Durable, Robust Superhydrophobic Fabric Coating" by Hua Zhou et al. in *Advanced Materials* 2012, 24, 2409-2412 discloses a superhydrophobic coating which includes polydimethylsiloxane, fluorinated alkyl silane functionalized silica nanoparticles, and fluorinated alkyl silane. The fluorinated alkyl silane functionalized silica nanoparticles are prepared by co-hydrolysis and co-condensation of tetraethyl orthosilicate under an alkaline condition in the presence of the fluorinated alkyl silane. Since the fluorinated alkyl silane is liable to undergo self-polymerization, the storage stability thereof is inferior and productivity of the fluorinated alkyl silane functionalized silica nanoparticles is unsatisfactory. In addition, since the fluorinated alkyl silane functionalized silica nanoparticles contain fluorine, which is harmful to human body, they cannot be used in medical products, cosmetic products, and the like.

CN 102952158 discloses a triazine type siloxane surface modifier of Formula I:

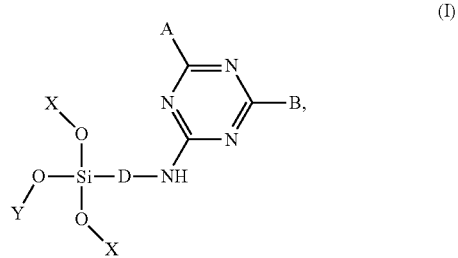

(I)

wherein A, B, D, X, and Y are as defined therein. The triazine type siloxane surface modifier is obtained through connection of siloxane and functional groups by using gradient reaction activity of cyanuric chloride. The triazine type siloxane surface modifier is applicable to hydrophobization or hydrophilization modification of an inorganic material surface.

SUMMARY

A first object of the disclosure is to provide a process for preparing a triazine-based precursor having superior storage stability.

A second object of the disclosure is to provide the triazine-based precursor prepared by the process.

A third object of the disclosure is to provide a method for producing a micro-particulate complex containing a far infrared-emissive silica particle using the triazine-based precursor.

A fourth object of the disclosure is to provide a micro-particulate complex containing a far infrared-emissive silica particle produced by the method.

According to a first aspect of the disclosure, there is provided a process for preparing a triazine-based precursor for producing a micro-particulate complex containing a far infrared-emissive silica particle. The process comprises steps of:

a) subjecting 2-4-6-trichloro-1,3,5-triazine and a first nucleophilic compound represented by a formula of H—X($R^1$)$_n$ to a displacement reaction in the presence of a first solvent at a first temperature range to form an intermediate represented by Formula (1)

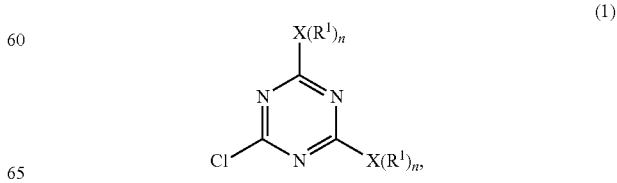

(1)

wherein
each X is a nucleophilic atom independently selected from the group consisting of N, O, and S,
each $R^1$ is independently selected from the group consisting of H, $C_1$-$C_{22}$ linear alkyl, and $C_1$-$C_{22}$ branched alkyl and is unsubstituted with amino, and
each n is independently 1 or 2,
with the proviso that
X is O or S and $R^1$ is not H when n is 1, and
X is N and at least one $R^1$ is not H when n is 2; and
b) subjecting the intermediate represented by Formula (1) and a second nucleophilic compound represented by a formula of H—NH—$R^2$—Si(O$R^3$)$_3$ to a further displacement reaction in the presence of a second solvent at a second temperature range higher than the first temperature range to form the triazine-based precursor represented by Formula (a),

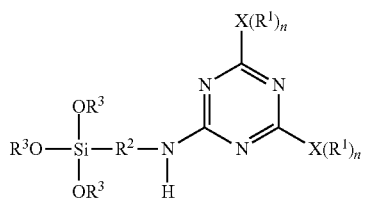

(a)

wherein
$R^2$ represents $C_2$-$C_4$ alkylene, and
each $R_3$ independently represents $C_1$-$C_2$ alkyl.

According to a second aspect of the disclosure, there is provided a triazine-based precursor prepared by the process according to the first aspect of the disclosure.

According to a third aspect of the disclosure, there is provided a method for producing a micro-particulate complex containing a far infrared-emissive silica particle. The method comprises a step of subjecting the triazine-based precursor according to the second aspect of the disclosure and tetra-alkyl orthosilicate to hydrolysis and polycondensation.

According to a fourth aspect of the disclosure, there is provided a micro-particulate complex containing a far infrared-emissive silica particle produced by the method according to the third aspect of the disclosure.

DETAILED DESCRIPTION

A process for preparing a triazine-based precursor for producing a micro-particulate complex containing a far infrared-emissive silica particle according to the disclosure comprises steps of:
a) subjecting 2-4-6-trichloro-1,3,5-triazine and a first nucleophilic compound represented by a formula of H—X($R^1$)$_n$ to a displacement reaction in the presence of a first solvent at a first temperature range to form an intermediate represented by Formula (1)

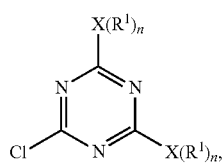

(1)

wherein
each X is a nucleophilic atom independently selected from the group consisting of N, O, and S,
each $R^1$ is independently selected from the group consisting of H, $C_1$-$C_{22}$ linear alkyl, and $C_1$-$C_{22}$ branched alkyl and is unsubstituted with amino, and
each n is independently 1 or 2,
with the proviso that
X is O or S and $R^1$ is not H when n is 1, and
X is N and at least one $R^1$ is not H when n is 2; and
b) subjecting the intermediate represented by Formula (1) and a second nucleophilic compound represented by a formula of H—NH—$R^2$—Si(O$R^3$)$_3$ to a further displacement reaction in the presence of a second solvent at a second temperature range higher than the first temperature range.

In certain embodiments, the first temperature range in step a) is up to 40° C.

In certain embodiments, the second temperature range in step b) is from 35° C. to 70° C.

In certain embodiments, step a) includes sub-steps of:
a1) subjecting 2-4-6-trichloro-1,3,5-triazine and the first nucleophilic compound to a first stage of the displacement reaction in the presence of the first solvent at a lower temperature ranging from 0° C. to 25° C. to form a pre-intermediate represented by Formula (i):

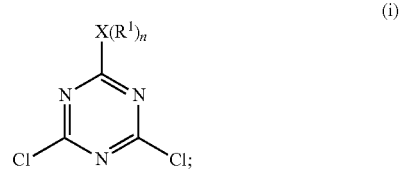

(i)

and
a2) subjecting the pre-intermediate represented by Formula (i) and the first nucleophilic compound to a second stage of the displacement reaction in the presence of the first solvent at an upper temperature which is higher than the lower temperature in sub-step a1) and which is from 15° C. to 40° C. to form the intermediate represented by Formula (1).

The first nucleophilic compound used in sub-step a1) may be the same as or different from that used in sub-step a2).

Examples of the first solvent include, but are not limited to, n-hexane, cyclohexane, dichloromethane, 1,2-dichloroethane, chloroform, acetone, ethyl acetate, tetrahydrofuran, ether, methanol, ethanol, and isopropanol. The examples may be used alone or in admixture of two or more thereof. The first solvent used in sub-step a1) may be the same as or different from that used in sub-step a2).

The first stage of the displacement reaction in sub-step a1) is conducted in the presence of a first basic agent. Examples of the first basic agent include, but are not limited to, sodium hydride, sodium bicarbonate, sodium carbonate, sodium hydroxide, potassium carbonate, potassium hydroxide, triethylamine, pyridine, N,N-diisopropylethylamine, 4-dimethylaminopyridine, 3-picoline, and 2,4,6-collidine. The examples may be used alone or in admixture of two or more thereof.

The second stage of the displacement reaction in sub-step a2) is conducted in the presence of a second basic agent, which may be the same as or different from the first basic agent used in the second stage of the displacement reaction in sub-step a1).

The second solvent used in step b) may be the same as or different from the first solvent used in step a).

The further displacement reaction in step b) is conducted in the presence of a third basic agent, which may be the same as or different from the first basic agent used in the second stage of the displacement reaction in sub-step a1).

A triazine-based precursor according to the disclosure is represented by Formula (a):

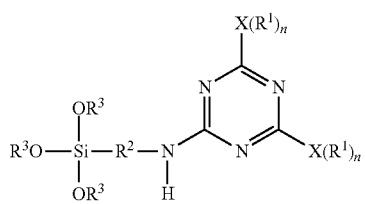

(a)

wherein
- each X is a nucleophilic atom independently selected from the group consisting of N, O, and S,
- each $R^1$ is independently selected from the group consisting of H, $C_1$-$C_{22}$ linear alkyl, and $C_1$-$C_{22}$ branched alkyl and is unsubstituted with amino,
- $R^2$ represents $C_2$-$C_4$ alkylene,
- each $R_3$ independently represents $C_1$-$C_2$ alkyl, and
- each n is independently 1 or 2, with the proviso that
- X is O or S and $R^1$ is not H when n is 1, and
- X is N and at least one $R^1$ is not H when n is 2.

A method for producing a micro-particulate complex containing a far infrared-emissive silica particle according to the disclosure comprises a step of subjecting the triazine-based precursor described above and tetra-alkyl orthosilicate to hydrolysis and polycondensation.

A non-limiting example of the tetra-alkyl orthosilicate is tetraethyl orthosilicate. In certain embodiments, the hydrolysis and the polycondensation are conducted at a temperature range from 25° C. to 60° C. for a period of from 24 hours to 72 hours.

A micro-particulate complex containing a far infrared-emissive silica particle according to the disclosure has a core-shell type configuration which includes a silica core and a shell formed by a plurality of radicals represented by

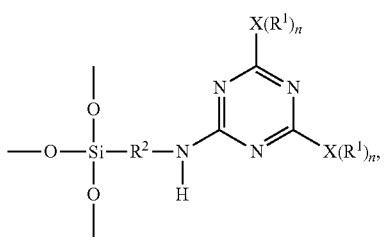

each of which bonds to the silica core via —O—.

As shown in Formula (a), due to a steric hindrance effect produced by a radical of

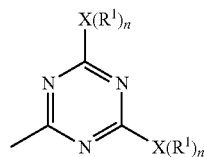

contained in the triazine-based precursor of Formula (a), the aforesaid self-polymerization which may occur in the prior art can be avoided so that the triazine-based precursor according to the disclosure is relatively stable. Therefore, the triazine-based precursor of Formula (a) and tetra-alkyl orthosilicate can be subjected to hydrolysis and polycondensation effectively to produce the micro-particulate complex according to the disclosure, which has the core-shell type configuration and thus has a desirably relatively narrow particle size distribution. In addition, since the triazine-based precursor according to the disclosure contains no halogen such as fluorine, the micro-particulate complex containing a far infrared-emissive silica particle produced using the triazine-based precursor is not harmful to human body and thus can be used for medical products, cosmetic products, and the like.

Since the far infrared-emissive silica particle contained in the micro-particulate complex according to the disclosure can emit far infrared radiation, the micro-particulate complex according to the disclosure can be used for medical products, for example, medical far infrared lamps; daily commodities, for examples, cosmetic products and textile products; health products, for example, heating pads and knee pads; and the like.

Examples of the disclosure will be described hereinafter. It is to be understood that these examples are exemplary and explanatory and should not be construed as a limitation to the disclosure.

EXAMPLE 1

Preparation of a Triazine-Based Precursor of Formula (a-1):

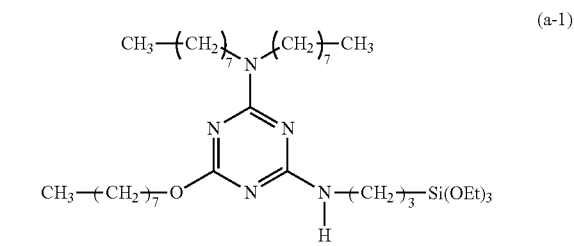

(a-1)

Step 1): A 100 ml reaction flask containing anhydrous methylene chloride (30 ml) therein was placed in an iced water bath at 0° C. Cyanuric chloride (1.84 g, 10 mmol) was added into the reaction flask and dissolved in anhydrous methylene chloride. Dioctylamine (2.41 g, 10 mmol) was then slowly added dropwise into the reaction flask, followed by reaction for 10 minutes. Triethylamine (1.01 g, 10 mmol) was then slowly added into the reaction flask, followed by further reaction for 20 minutes. The content in the reaction flask was then extracted twice using an aqueous sodium hydroxide solution (0.5M, 30 ml in total). Combined organic extracts were collected and further extracted using water (50 ml), followed by dryness using anhydrous magnesium sulphate to obtain a solution. The solution was concentrated under a reduced pressure to remove methylene chloride therefrom to obtain 2,4-dichloro-6-dioctylamino-1,3,5-triazine (3.69 g, 9.5 mmol).

Step 2): A 50 ml reaction flask containing anhydrous methylene chloride (20 ml) and 2,4-dichloro-6-dioctylamino-1,3,5-triazine (3.88 g, 10 mmol) therein was placed in an iced water bath at 0° C. Sodium hydride (60%, 0.4 g, 10 mmol) was combined with 1-octanol (1.3 g, 10 mmol), followed by reaction for 2 minutes to form a reaction mixture. The reaction mixture was slowly added into the reaction flask, followed by reaction in the iced water bath for 10 minutes and further reaction at room temperature for 12 hours. The content in the reaction flask was then extracted twice using an aqueous sodium hydroxide solution (0.5M, 30 ml in total). Combined organic layers were collected and further extracted using water (50 ml). An organic layer thus formed was collected and added with anhydrous magnesium sulphate to remove water therefrom, followed by filtration to obtain a filtrate. The filtrate was concentrated under a reduced pressure to remove methylene chloride therefrom to obtain 2-chloro-4-dioctylamino-6-octyloxy-1,3,5-triazine (4.54 g, 9.4 mmol).

Step 3): 2-chloro-4-dioctylamino-6-octyloxy-1,3,5-triazine (4.83 g, 10 mmol) was dissolved in tetrahydrofuran (50 ml), followed by addition of 3-(triethoxysilyl)propylamine (2.44 g, 11 mmol) and N,N-diisopropylethylamine (2.6 g, 20 mmol) and reaction at 65° C. for 48 hours. Tetrahydrofuran was then removed via condensation under a reduced pressure to obtain a reaction mixture. The reaction mixture was dissolved in methylene chloride (30 ml) and then extracted twice using an aqueous sodium hydroxide solution (0.5M, 30 ml in total). Combined organic extracts were collected and further extracted using water (50 ml), followed by dryness using anhydrous magnesium sulphate to obtain a solution. The solution was concentrated under a reduced pressure to remove methylene chloride therefrom to obtain a concentrate. The concentrate was purified by column chromatography on a silica gel column (diameter: 2.6 cm, length: 15 cm) using a 5:1 v/v mixture of hexane and tetrahydrofuran as an eluent to obtain 2-dioctylamino-4-octyloxy-6-(3-triethoxysilylpropyl)amino-1,3,5-triazine (4.48 g, 6.7 mmol, yield: 59.8%).

Spectrum analysis for 2-dioctylamino-4-octyloxy-6-(3-triethoxysilylpropyl)amino-1,3,5-triazine: $^1$H NMR (300 MHz, CDCl$_3$, δ (ppm): 0.64 (t, J=8.4 Hz, 2H, CH$_2$—Si), 0.86 (t, J=6.3 Hz, 9H, 3×CH$_3$), 1.20 (t, J=6.9 Hz, 9H, 3×CH$_3$—COSi), 1.26 (s, broad, 30H, 15×CH$_2$), 1.55 (s, broad, 4H, 2×CH$_2$—CN), 1.60~1.78 (m, 4H, CH$_2$—CSi+CH$_2$—CO), 3.33~3.51 (m, 6H, 3×CH$_2$—N), 3.80 (q, J=6.9 Hz, 6H, 3×CH$_2$—OSi), 4.21 (s, broad, 2H, CH$_2$—O), 5.05 (t, J=5.7 Hz, 1H, N—H); MS: m/z 668.51 (M+H)$^+$.

EXAMPLE 2

Preparation of a Triazine-Based Precursor of Formula (a-2):

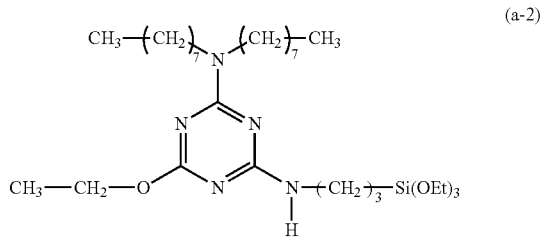

The procedure for Example 1 was repeated except that in step 2), 1-octanol was replaced with ethanol to obtain 2-chloro-4-dioctylamino-6-ethyloxy-1,3,5-triazine and that in step 3), 2-chloro-4-dioctylamino-6-octyloxy-1,3,5-triazine was replaced with 2-chloro-4-dioctylamino-6-ethyloxy-1,3,5-tri-azine to obtain 2-dioctylamino-4-ethyloxy-6-(3-triethoxysilylpropyl)amino-1,3,5-triazine (yield: 47.0%) accordingly.

Spectrum analysis for 2-dioctylamino-4-ethyloxy-6-(3-triethoxysilylpropyl)amino-1,3,5-triazine: $^1$H NMR (300 MHz, CDCl$_3$, δ (ppm): 0.62 (t, J=8.1 Hz, 2H, CH$_2$—Si), 0.86 (t, J=6.3 Hz, 6H, 2×CH$_3$), 1.20 (t, J=6.9 Hz, 9H, 3×CH$_3$—COSi), 1.27 (s, broad, 23H, 10×CH$_2$+CH$_3$), 1.55 (s, broad, 4H, 2×CH$_2$—CN), 1.60~1.78 (m, 2H, CH$_2$—CSi), 3.33~3.51 (m, 6H, 3×CH$_2$—N), 3.80 (q, J=6.9 Hz, 6H, 3×CH$_2$—OSi), 4.25 (s, broad, 2H, CH$_2$—O), 5.05 (t, J=5.7 Hz, 1H, N—H); MS: m/z 584.79 (M+H)$^+$.

EXAMPLE 3

Preparation of a Triazine-Based Precursor of Formula (a-3):

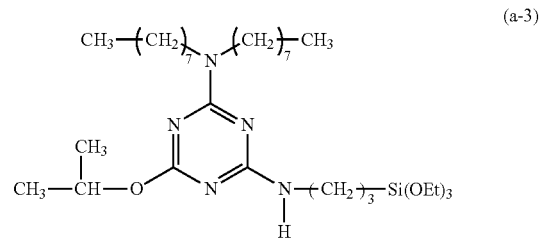

The procedure for Example 1 was repeated except that in step 2), 1-octanol was replaced with isopropanol to obtain 2-chloro-4-dioctylamino-6-isopropyloxy-1,3,5-triazine and that in step 3), 2-chloro-4-dioctylamino-6-octyloxy-1,3,5-triazine was replaced with 2-chloro-4-dioctylamino-6-isopropyloxy-1,3,5-triazine to obtain 2-dioctylamino-4-isopropyloxy-6-(3-triethoxysilylpropyl)amino-1,3,5-triazine (yield: 42.1%) accordingly.

Spectrum analysis for 2-dioctylamino-4-isopropyloxy-6-(3-triethoxysilylpropyl)-amino-1,3,5-triazine: $^1$H NMR (300 MHz, CDCl$_3$), δ (ppm): 0.61 (t, J=8.1 Hz, 2H, CH$_2$—Si), 0.85 (t, J=6.3 Hz, 6H, 2×CH$_3$), 1.19 (t, J=6.9 Hz, 9H, 3×CH$_3$—COSi), 1.31 (s, broad, 26H, 13×CH$_2$), 1.55 (s, broad, 4H, 2×CH$_2$—CN), 1.69 (m, J=6.6 Hz, 2H, CH$_2$—CSi), 3.35 (q, J=6.3 Hz, 2H, 3×CH$_2$—N), 3.45 (q, J=6.3 Hz, 4H, 2×CH$_2$—N), 3.77 (q, J=6.9 Hz, 6H, 3×CH$_2$—OSi), 5.37 (s, broad, 1H, CH—O), 6.323 (s, 1H, N—H); MS: m/z 598.83 (M+H)$^+$ (theoretical value: 597.465).

EXAMPLE 4

Preparation of a Triazine-Based Precursor of Formula (a-4)

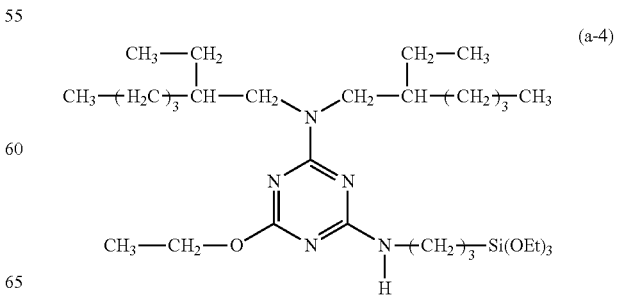

The procedure for Example 1 was repeated except that in step 1), dioctylamine was replaced with di(2-ethylhexyl)amine to obtain 2,4-dichloro-6-di(2-ethylhexyl)amino-1,3,5-triazine, that in step 2), 1-octanol was replaced with ethanol to obtain 2-chloro-4-di(2-ethylhexyl)amino-6-ethyloxy-1,3,5-triazine, and that in step 3), 2-chloro-4-dioctylamino-6-octyloxy-1,3,5-triazine was replaced with 2-chloro-4-di(2-ethylhexyl)amino-6-ethyloxy-1,3,5-triazine to obtain 2-di(2-ethylhexyl)amino-4-ethyloxy-6-(3-triethoxysilylpropyl)amino-1,3,5-triazine (yield: 41.0%) accordingly.

Spectrum analysis for 2-di(2-ethylhexyl)amino-4-ethyloxy-6-(3-triethoxysilylpropyl)amino-1,3,5-triazine: $^1$H NMR (300 MHz, CDCl$_3$), δ (ppm): 0.66 (t, J=8.1 Hz, 2H, CH$_2$—Si), 0.86 (t, J=6.9 Hz, 12H, 4×CH$_3$), 1.22 (t, J=6.9 Hz, 9H, 3×CH$_3$—COSi), 1.26 (s, broad, 16H, 8×CH$_2$), 1.34 (t, J=7.5 Hz, 3H, 1×CH$_3$), 1.64~1.80 (m, 4H, CH$_2$—CSi+ 2×CH), 3.37~3.44 (m, 6H, 3×CH$_2$—N), 3.81 (q, J=6.9 Hz, 6H, 3×CH$_2$—OSi), 4.31 (t, J=6.6 Hz, 2H, CH$_2$—O), 4.95 (s, broad, 1H, H—N); MS: m/z 584.92 (M+H)$^+$.

EXAMPLE 5

Preparation of a Triazine-Based Precursor of Formula (a-5):

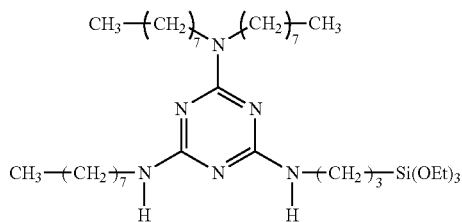

(a-5)

The procedure for Example 1 was repeated except that in step 2), 1-octanol was replaced with 1-octylamine to obtain 2-chloro-4-octylamino-6-dioctylamino-1,3,5-triazine and that in step 3), 2-chloro-4-dioctylamino-6-octyloxy-1,3,5-triazine was replaced with 2-chloro-4-octylamino-6-dioctylamino-1,3,5-triazine to obtain 2-octylamino-4-dioctylamino-6-(3-triethoxysilylpropyl)amino-1,3,5-triazine (yield: 49.3%) accordingly.

Spectrum analysis for 2-octylamino-4-dioctylamino-6-(3-triethoxysilylpropyl)amino-1,3,5-triazine: $^1$H NMR (300 MHz, CDCl$_3$), δ (ppm): 0.68 (t, J=8.7 Hz, 2H, CH$_2$—Si), 0.88 (t, J=6.3 Hz, 9H, 3×CH$_3$), 1.21 (t, J=6.9 Hz, 9H, 3×CH$_3$—COSi), 1.26 (s, broad, 30H, 15×CH$_2$), 1.51~1.80 (m, 8H, CH$_2$—CSi+3×CH$_2$—CN), 3.33~3.51 (m, 8H, 4×CH$_2$—N), 3.81 (q, J=6.9 Hz, 6H, 3×CH$_2$—OSi), 5.01 (s, broad, 1H, H—N), 5.35 (t, J=4.8 Hz, 1H, H—N); MS: m/z 667.35 (M+H)$^+$.

EXAMPLE 6

Preparation of a Triazine-Based Precursor of Formula (a-6):

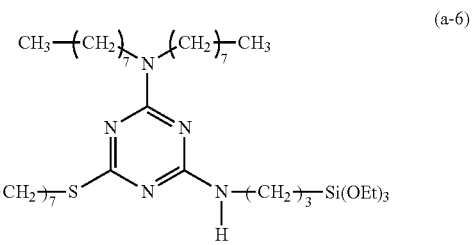

(a-6)

The procedure for Example 1 was repeated except that in step 2), 1-octanol was replaced with 1-octanethiol to obtain 2-chloro-4-dioctylamino-6-octylthio-1,3,5-triazine and that in step 3), 2-chloro-4-dioctylamino-6-octyloxy-1,3,5-triazine was replaced with 2-chloro-4-dioctylamino-6-octylthio-1,3,5-triazine to obtain 2-dioctylamino-4-octylthio-6-(3-triethoxysilylpropyl)amino-1,3,5-triazine (yield: 53.3%) accordingly.

Spectrum analysis for 2-dioctylamino-4-octylthio-6-(3-triethoxysilylpropyl)amino-1,3,5-triazine: $^1$H NMR (300 MHz, CDCl$_3$), δ (ppm): 0.65 (t, J=8.4 Hz, 2H, CH$_2$—Si), 0.88 (t, J=6.3 Hz, 9H, 3×CH$_3$), 1.22 (t, J=6.9 Hz, 9H, 3×CH$_3$—COSi), 1.27 (s, broad, 30H, 15×CH$_2$), 1.42 (s, broad, 4H, 2×CH$_2$—CN), 1.60~1.78 (m, 4H, CH$_2$—CSi+ CH$_2$—CO), 3.01 (t, J=7.2 Hz, 2H, CH$_2$—S), 3.36~3.51 (m, 6H, 3×CH$_2$—N), 3.81 (q, J=6.9 Hz, 6H, 3×CH$_2$—OSi), 5.01 (t, J=5.7 Hz, 1H, H—N); MS: m/z 683.78 (M)$^+$.

EXAMPLE 7

Preparation of a Triazine-Based Precursor of Formula (a-7):

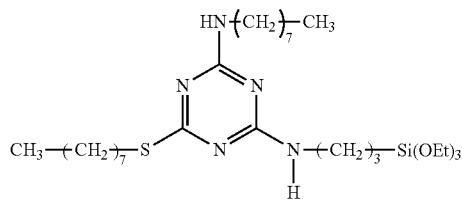

(a-7)

The procedure for Example 1 was repeated except that in step 1), dioctylamine was replaced with 1-octylamine to obtain 2,4-dichloro-octylamino-1,3,5-triazine, that in step 2), 1-octanol was replaced with 1-octanethiol to obtain 2-chloro-4-octylamino-6-octylthio-1,3,5-triazine, and that in step 3), 2-chloro-4-dioctylamino-6-octyloxy-1,3,5-triazine was replaced with 2-chloro-4-dioctylamino-6-octylthio-1,3,5-triazine to obtain 2-octylamino-4-octylthio-6-(3-triethoxysilylpropyl)amino-1,3,5-triazine (yield: 43.1%) accordingly.

Spectrum analysis for 2-octylamino-4-octylthio-6-(3-triethoxysilylpropyl)amino-1,3,5-triazine: $^1$H NMR (300 MHz, CDCl$_3$), δ (ppm): 0.66 (t, J=8.4 Hz, 2H, CH$_2$—Si), 0.88 (t, J=6.3 Hz, 6H, 2×CH$_3$), 1.23 (t, J=7.2 Hz, 9H, 3×CH$_3$—COSi), 1.26 (s, broad, 20H, 10×CH$_2$), 1.48~1.78 (m, 6H, CH$_2$—CSi+CH$_2$—CN+CH$_2$—CS), 3.03 (t, J=7.2 Hz, 2H, CH$_2$—S), 3.34~3.51 (m, 4H, 2×CH$_2$—N), 3.82 (q, J=6.6 Hz, 6H, 3×CH$_2$—OSi), 5.03 (s, broad, 1H, H—N), 5.35 (t, J=5.1, 1H, H—N); MS: m/z 571.83 (M)$^+$.

EXAMPLE 8

Preparation of a Triazine-Based Precursor of Formula (a-8):

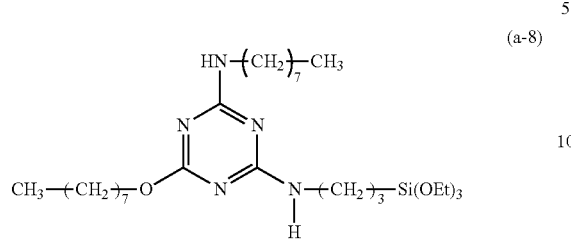
(a-8)

The procedure for Example 1 was repeated except that in step 1), dioctylamine was replaced with 1-octylamine to obtain 2,4-dichloro-octylamino-1,3,5-triazine, that in step 2), 2,4-dichloro-6-dioctylamino-1,3,5-triazine was replaced with 2,4-dichloro-6-octylamino-1,3,5-triazine to obtain 2-chloro-4-octylamino-6-octyloxy-1,3,5-triazine, and that in step 3), 2-chloro-4-dioctylamino-6-octyloxy-1,3,5-triazine was replaced with 2-chloro-4-octylamino-6-octyloxy-1,3,5-triazine to obtain 2-octylamino-4-octyloxy-6-(3-triethoxysilylpropyl)amino-1,3,5-triazine (yield: 35.2%) accordingly.

Spectrum analysis for 2-octylamino-4-octyloxy-6-(3-triethoxysilylpropyl)amino-1,3,5-triazine: $^1$H NMR (300 MHz, CDCl$_3$), δ (ppm): 0.69 (t, J=7.2 Hz, 2H, CH$_2$—Si), 0.88 (t, J=6.6 Hz, 6H, 2×CH$_3$), 1.22 (t, J=6.9 Hz, 9H, 3×CH$_3$—COSi), 1.26 (s, broad, 20H, 10×CH$_2$), 1.49~1.8. (m, 6H, CH$_2$—CSi+2×CH$_2$—CO), 3.22~3.51 (m, 4H, 2×CH$_2$—N), 3.81 (q, J=6.9 Hz, 6H, 3×CH$_2$—OSi), 4.16~4.39 (m, 2H, CH$_2$—O), 5.01 (s, broad, 1H, H—N), 5.35 (t, J=5.1, 1H, H—N); MS: m/z 556.54 (M+H)$^+$.

EXAMPLE 9

Preparation of a Triazine-Based Precursor of Formula (a-9):

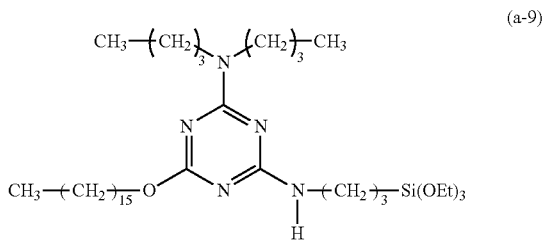
(a-9)

The procedure for Example 1 was repeated except that in step 1), dioctylamine was replaced with dibutylamine to obtain 2,4-dichloro-dibutylamino-1,3,5-triazine, that in step 2), 1-octane was replaced with 1-hexadecanol to obtain 2-chloro-4-dibutylamino-6-hexadecyloxy-1,3,5-triazine, and that in step 3), 2-chloro-4-dioctylamino-6-octyloxy-1,3,5-triazine was replaced with 2-chloro-4-dibutylamino-6-hexadecyloxy-1,3,5-triazine to obtain 2-dibutylamino-4-hexadecyloxy-6-(3-triethoxysilylpropyl)amino-1,3,5-triazine (yield: 38.3%) accordingly.

Spectrum analysis for 2-dibutylamino-4-hexadecyloxy-6-(3-triethoxysilylpropyl)amino-1,3,5-triazine: $^1$H NMR (300 MHz, CDCl$_3$), δ (ppm): 0.64 (t, J=8.4 Hz, 2H, CH$_2$—Si), 0.88 (t, J=6.9 Hz, 9H, 3×CH$_3$), 1.22 (t, J=6.9 Hz, 9H, 3×CH$_3$—COSi), 1.31 (s, broad, 30H, 15×CH$_2$), 1.51~1.73 (m, 8H, 2×CH$_2$—CN)+CH$_2$—CSi+CH$_2$—CO), 3.33~3.58 (m, 6H, 3×CH$_2$—N), 3.81 (q, J=6.9 Hz, 6H, 3×CH$_2$—OSi), 4.21 (s, broad, 2H, CH$_2$—O), 5.7 (t, J=5.1 Hz, 1H, H—N); MS: m/z 568.71 (M+H)$^+$.

EXAMPLE 10

Preparation of a Triazine-Based Precursor of Formula (a-10):

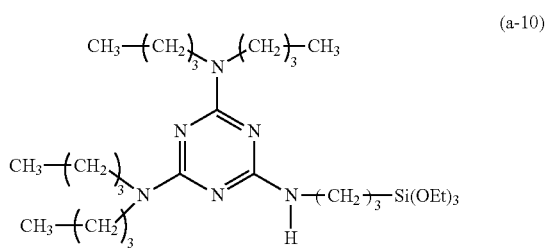
(a-10)

Step 1): A 100 ml reaction flask containing anhydrous methylene chloride (50 ml) therein was placed in an iced water bath at 0° C. Cyanuric chloride (1.84 g, 10 mmol) was added into the reaction flask and dissolved in anhydrous methylene chloride. Dibutylamine (2.81 g, 22 mmol) was then slowly added dropwise into the reaction flask, followed by reaction for 20 minutes. Triethylamine (2.53 g, 25 mmol) was then slowly added into the reaction flask, followed by further reaction for 20 minutes.

Step 2): The reaction was continued at room temperature (about 27° C.) for additional 12 hours. The content in the reaction flask was then extracted twice using an aqueous sodium hydroxide solution (0.5M, 60 ml in total). Combined organic extracts were collected and further extracted using water (50 ml), followed by dryness using anhydrous magnesium sulphate to obtain a solution. The solution was concentrated under a reduced pressure to remove methylene chloride therefrom to obtain 2-chloro-4,6-bis(dibutylamino)-1,3,5-triazine (3.37 g, 9.2 mmol).

Step 3): 2-chloro-4,6-bis(dibutylamino)-1,3,5-triazine (3.67 g, 10 mmol) was dissolved in tetrahydrofuran (50 ml), followed by addition of 3-(triethoxysilyl)propylamine (2.44 g, 11 mmol) and N,N-diisopropylethylamine (2.6 g, 20 mmol) and reaction at 50° C. for 24 hours. Tetrahydrofuran was then removed via condensation under a reduced pressure to obtain a reaction mixture. The reaction mixture was added with methylene chloride (30 ml) and extracted twice using an aqueous sodium hydroxide solution (0.5M, 30 ml in total). Combined organic extracts were collected and further extracted using water (50 ml), followed by dryness using anhydrous magnesium sulphate to obtain a solution. The solution was concentrated under a reduced pressure to remove methylene chloride therefrom to obtain a concentrate. The concentrate was purified by column chromatography on a silica gel column (diameter: 2.6 cm, length: 15 cm) using a 5:1 v/v mixture of hexane and tetrahydrofuran as an eluent to obtain 2,4-bis(dibutylamino)-6-(3-triethoxysilylpropyl)amino-1,3,5-triazine (1.99 g, 3.6 mmol, yield: 33.1%).

Spectrum analysis for 2,4-bis(dibutylamino)-6-(3-triethoxysilylpropyl)amino-1,3,5-triazine: $^1$H NMR (300 MHz, CDCl$_3$), δ (ppm): 0.67 (t, J=6.3 Hz, 2H, CH$_2$—Si), 0.92 (t, J=7.2 Hz, 12H, 4×CH$_3$), 1.21 (t, J=6.9 Hz, 9H, 3×CH$_3$—COSi), 1.30 (q, J=7.5 Hz, 8H, 4×CH$_2$—CN), 1.60—1.71 (m, 10H, CH$_2$—CSi+4×CH$_2$—CN), 3.30 (q, J=6.6 Hz, 2H, CH$_2$—N), 3.43 (t, J=7.8 Hz, 8H, 4×CH$_2$—N), 3.81 (q, J=6.9 Hz, 6H, 3×CH$_2$—OSi), 4.73 (t, J=6.0 Hz, 1H, H—N); MS: m/z 555.79 (M+H)$^+$.

EXAMPLE 11

Preparation of a Triazine-Based Precursor of Formula (a-11):

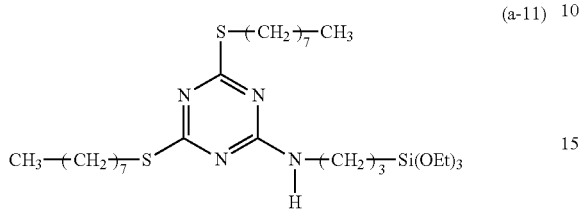

(a-11)

The procedure for Example 10 was repeated except that in step 1), dibutylamine was replaced with 1-octanethiol and triethylamine was replaced with N,N-diisopropylethylamine, that in step 2), 2-chloro-4,6-di(octylthio)-1,3,5-triazine was obtained, and that in step 3), 2-chloro-4,6-bis(dibutylamino)-1,3,5-triazine was replaced with 2-chloro-4,6-di(octylthio)-1,3,5-triazine to obtain 2,4-di(octylthio)-6-(3-triethoxysilylpropyl)amino-1,3,5-triazine (yield: 58.3%) accordingly.

Spectrum analysis for 2,4-di(octylthio)-6-(3-triethoxysilylpropyl)amino-1,3,5-triazine: $^1$H NMR (300 MHz, CDCl$_3$), δ (ppm): 0.65 (t, J=8.4 Hz, 2H, CH$_2$—Si), 0.87 (t, J=7.2 Hz, 6H, 2×CH$_3$), 1.22 (t, J=7.2 Hz, 9H, 3×CH$_3$—COSi), 1.271 (s, broad, 16H, 8×CH$_2$), 1.34~1.49 (m, 4H, 2×CH$_2$), 1.67~1.79 (m, 6H, CH$_2$—CSi+2×CH$_2$—CS), 3.05 (t, J=6.6 Hz, 4H, 2×CH$_2$—S), 3.41 (q, J=6.3 Hz, 2H, CH$_2$—N), 3.82 (q, J=6.6 Hz, 6H, 3×CH$_2$—OSi), 5.46 (s, broad, 1H, H—N); MS: m/z 589.90 (M+H)$^+$.

EXAMPLE 12

Preparation of a Triazine-Based Precursor of Formula (a-12):

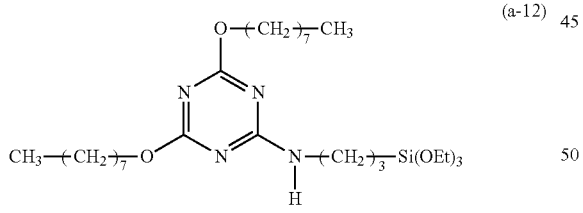

(a-12)

The procedure for Example 10 was repeated except that in step 1), dibutylamine was replaced with 1-octanol and triethylamine was replaced with sodium hydride, that in step 2), 2-chloro-4,6-di(octyloxy)-1,3,5-triazine was obtained, and that in step 3), 2-chloro-4,6-bis(dibutylamino)-1,3,5-triazine was replaced with 2-chloro-4,6-di(octyloxy)-1,3,5-triazine to obtain 2,4-di(octyloxy)-6-(3-triethoxysilylpropyl)amino-1,3,5-triazine (yield: 68.4%) accordingly.

Spectrum analysis for 2,4-di(octyloxy)-6-(3-trethoxysilylpropyl)amino-1,3,5-triazine: $^1$H NMR (300 MHz, CDCl$_3$, 298K), δ (ppm): 0.66 (t, J=8.4 Hz, 2H, CH$_2$—Si), 0.88 (t, J=8.4 Hz, 6H, 2×CH$_3$), 1.23 (t, J=6.9 Hz, 9H, 3×CH$_3$—COSi), 1.28 (s, broad, 16H, 8×CH$_2$), 1.34~1.49 (m, 4H, 2×CH$_2$), 1.67~1.79 (m, 6H, CH$_2$—CSi+2×CH$_2$—CO), 3.44 (q, J=6.3 Hz, 2H, CH$_2$—N), 3.82 (q, J=6.6 Hz, 6H, 3×CH$_2$—OSi), 4.3 (t, J=8.1 Hz, 4H, 2×CH$_2$—O), 5.42 (t, J=5.1, 1H, H—N); MS: m/z 557.83 (M+H)$^+$.

EXAMPLE 13

Preparation of a Triazine-Based Precursor of Formula (a-13):

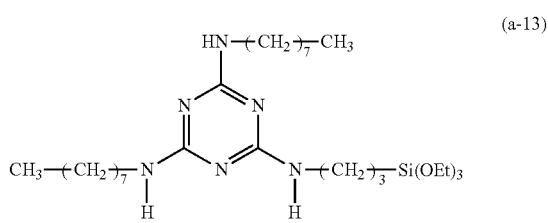

(a-13)

The procedure for Example 10 was repeated except that in step 1), dibutylamine was replaced with 1-octylamine, that in step 2), 2-chloro-4,6-di(octylamino)-1,3,5-triazine was obtained, and that in step 3), 2-chloro-4,6-bis(dibutylamino)-1,3,5-triazine was replaced with 2-chloro-4,6-di(octylamino)-1,3,5-tri-azine to obtain 2,4-di(octylamino)-6-(3-triethoxy-silylpropyl)amino-1,3,5-triazine (yield: 52.3%) accordingly.

Spectrum analysis for 2,4-di(octylamino)-6-(3-triethoxysilylpropyl)amino-1,3,5-triazine: $^1$H NMR (300 MHz, CDCl$_3$), δ (ppm): 0.66 (t, J=8.4 Hz, 2H, CH$_2$—Si), 0.87 (t, J=6.3 Hz, 6H, 2×CH$_3$), 1.21 (t, J=6.9 Hz, 9H, 3×CH$_3$—COSi), 1.28 (s, broad, 20H, 10×CH$_2$), 1.41~1.79 (m, 6H, CH$_2$—CSi+2×CH$_2$—CN), 3.32 (s, broad, 6H, 3×CH$_2$—N), 3.81 (q, J=6.9 Hz, 6H, 3×CH$_2$—OSi), 4.84 (s, broad, 3H, 3×H—N); MS: m/z 555.44 (M+H)$^+$.

APPLICATION EXAMPLE 1

2-dioctylamino-4-octyloxy-6-(3-triethoxysilylpropyl) amino-1,3,5-triazine (6.68 g, 10 mmol) obtained in Example 1, tetraethyl orthosilicate (20.8 g, 100 mmol), and ethanol (30 ml) were stirred evenly for 3 minutes, followed by slow addition of an aqueous ammonia solution (35%, 22 ml), reaction for 24 hours, and filtration to obtain a filter cake. The filter cake was washed twice with hot water and then dried to obtain a particulate product (6.5 g, yield: 58.6%) of micro-particulate complex containing a far infrared-emissive silica particle.

APPLICATION EXAMPLE 2

The procedure for Application Example 1 was repeated except that 2-dioctylamino-4-octyloxy-6-(3-triethoxysilylpropyl)amino-1,3,5-triazine was replaced with 2-dioctylamino-4-ethyloxy-6-(3-triethoxysilylpropyl)amino-1,3,5-triazine (5.8 g, 10 mmol) obtained in Example 2 to obtain a particulate product (6.3 g, yield: 57.4%) of micro-particulate complex containing a far infrared-emissive silica particle.

APPLICATION EXAMPLE 3

The procedure for Application Example 1 was repeated except that 2-dioctylamino-4-octyloxy-6-(3-triethoxysilylpropyl)amino-1,3,5-triazine was replaced with 2-dioctylamino-4-isopropyloxy-6-(3-triethoxysilylpropyl)amino-1, 3,5-triazine (5.9 g, 10 mmol) obtained in Example 2 to obtain a particulate product (5.9 g, yield: 53.9%) of microparticulate complex containing a far infrared-emissive silica particle.

COMPARATIVE APPLICATION EXAMPLE 1

Tetraethyl orthosilicate (20.8 g, 100 mmol) and ethanol (30 ml) were stirred evenly for 3 minutes, followed by slow addition of an aqueous ammonia solution (35%, 22 ml), reaction for 24 hours, and filtration to obtain a filter cake. The filter cake was washed twice with hot water and then dried to obtain a particulate product (5.1 g, yield: 85%) of silica particles.

Evaluation Items:

1. Measurement of Particle Size (μm):

The particulate product obtained in each of Application Example 1, Application Example 2, and Comparative Application Example 1 was dispersed in ethanol, and the particle size thereof was measured using a particle size and zeta potential analyzer (Otsuka Electronics, NanoPlus). The results are shown in Table 1.

2. Far Infrared Emissivity (%):

A detection film having a length of about 13 mm, a width of about 13 mm, and a thickness of less than 2 mm was prepared from the particulate product obtained in each of Application Example 1, Application Example 2, and Comparative Application Example 1. The detection film was subjected to FTIR analysis using a Bruker Optics FTIR spectrometer (Model #VERTEX 70) under conditions which include a detection temperature of 40° C., an environment temperature of 25±3° C., a relative humidity of 60±10%, and a detection wavelength range of from 4 μm to 14 μm. The results are shown in Table 1.

3. Skin Irritation Test:

The skin irritation test was conducted according to ASTM F719-81 and ISO 10993-10. Back hair of a New Zealand white rabbit was removed by shaving. The rabbit having intact shaved back skin without scratch and skin disease was used for the test. The particulate product (2 g) obtained in each of Application Example 1, Application Example 2, and Comparative Application Example 1 was mixed with normal saline (10 ml) to prepare a test sample (concentration: 0.2 g/mL). Two pieces of cotton gauze were respectively immersed into the test sample (0.5 mL) and normal saline (0.5 mL, as a control) for 72 hours, and were then disposed separately on the intact shaved back shin of the New Zealand white rabbit and fixed with a breathable bandage. The pieces of cotton gauze were removed after 4 hours. The intact shaved back skin of the New Zealand white rabbit was observed at 1 hour, 24 hours, 48 hours, and 72 hours to see whether or not erythema or edema appeared. The results are shown in Table 1.

4. Cytotoxicity Test A:

The cytotoxicity test A was performed using an agar diffusion test. Mouse fibroblast cells (L929 cells, CCRC 60091 NCTN Clone 929, strain L) were plated in each well of a 6-well plate, followed by addition of a minimum essential medium containing serum (10%) and an antibiotic (1%) into each well of the 6-well plate for incubation of the cells. When a sub-confluent cell layer was formed in each well of the 6-well plate, additional agar (1.5%, 2 mL) was added into each well of the 6-well plate. After the agar was solidified, a test sample was disposed in one well of the 6-well plate, and the remaining wells of the 6-well plate were not added with the test sample and were used as controls. The 6-well plate was disposed in an incubator containing carbon dioxide (5%) at 37° C. for incubation of the cells for 24 hours. The cells were then stained with a neutral red solution and the number of living cells was counted. The cytotoxicity test A was performed according to ISO10993-5 and ASTM F895-11. Cytotoxicity was estimated as a response index (zone index/lysis index). It was estimated as an average from three replicated test results. The lower the response index, the lower the cytotoxicity. The test sample used in the cytotoxicity test A was prepared by mixing the particulate product (0.2 g) obtained in each of Application Example 1, Application Example 2, and Comparative Application Example 1 with the minimum essential medium containing serum (10%) and an antibictic (1%) to prepare the test sample having a concentration of 0.2 g/mL. In the test for the particulate product obtained in Application Example 1, the response index of the controls was 0/0. In the test for the particulate product obtained in Application Example 2, the response index of the controls was 0/0. In the test for the particulate product obtained in Comparative Application Example 1, the response index of the controls was 5/5. The results for the cytotoxicity test A are shown in Table 1.

5. Cytotoxicity Test B:

The cytotoxicity test B was performed using an MTT assay. Mouse fibroblast cells (L929 cells, CCRC 60091 NCTN Clone 929, strain L) were plated in each well of a 96-well plate, followed by addition of a minimum essential medium containing serum (10%) and an antibiotic (1%) in each well of the 96-well plate for incubation of the cells. When a sub-confluent cell layer was formed in each well of the 96-well plate, a test sample (0.1 mL) was disposed in some wells of the 96-well plate, and the remaining wells of the 96-well plate were not added with the test sample and were used as controls. The 96-well plate was disposed in an incubator containing carbon dioxide (5%) at 37° C. for incubation of the cells for 24 hours. Cell viability was determined by the MTT assay. It was estimated as an average from three replicated assay results. The test sample used in the cytotoxicity test B was prepared by mixing the particulate product (0.2 g) obtained in each of Application Example 1, Application Example 2, and Comparative Application Example 1 with the minimum essential medium containing serum (10%) and an antibiotic (1%) to prepare the test sample having a concentration of 0.2 g/mL. In the test for the particulate product obtained in Application Example 1, the cell viability of the controls was 73.3±5.7%. In the test for the particulate product obtained in Application Example 2, the cell viability of the controls was 102.9±6.8%. In the test for the particulate product obtained in Comparative Application Example 1, the cell viability of the controls was 35.4±4.9. The results for the cytotoxicity test B are shown in Table 1.

TABLE 1

| Micro-particulate complex containing a far infrared-emissive silica particle | Appl. Ex. 1 | Appl. Ex. 2 | Appl. Ex. 3 | Comp. Appl. Ex. 1 |
|---|---|---|---|---|
| Triazine-based precursor | Ex. 1 | Ex. 2 | Ex. 3 | — |
|  | | $Si(OC_2H_5)_4$ | | |
| Particle size (μm) | 145.4~280.9 | 2.1~51.4 | 3.2~20.8 | 24.6~45.4 |
| Far infrared emissivity (%) | 0.88 | 0.87 | 0.85 | 0.82 |
| Skin irritation test | No erythema No edema | No erythema No edema | No erythema No edema | — |
| Cytotoxicity test A | No RI: 0/0 | No RI: 0/0 | No RI: 0/0 | Yes RI: 5/5 |
| Cytotoxicity test B (Cell viability) | No 73.3 ± 15.7 | No 102.9 ± 6.8% | No 70.64 ± 3.54 | Yes 35.4 ± 4.9% |

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for producing a micro-particulate complex containing a far infrared-emissive silica particle, comprising a step of subjecting a triazine-based precursor represented by Formula (a) and tetra-alkyl orthosilicate to hydrolysis and polycondensation,

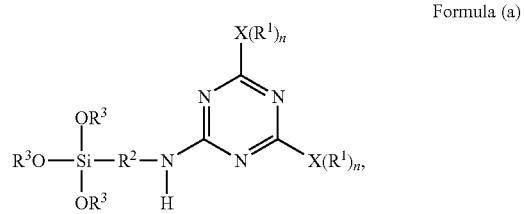

Formula (a)

wherein
each X is a nucleophilic atom independently selected from the group consisting of N, O, and S;
Xs are different from each other;
each $R^1$ is independently selected from the group consisting of H and $C_1$-$C_{22}$ linear or branched unsubstituted alkyl;
$R^2$ represents $C_2$-$C_4$ alkylene;
each $R_3$ independently represents $C_1$-$C_2$ alkyl; and
each n is independently 1 or 2,
with the proviso that
X is O or S and $R^1$ is not H when n is 1, and
X is N and at least one $R^1$ is not H when n is 2.

2. The method according to claim 1, wherein the tetra-alkyl orthosilicate is tetraethyl orthosilicate.

* * * * *